(12) United States Patent
Fletcher et al.

(10) Patent No.: US 7,381,725 B2
(45) Date of Patent: Jun. 3, 2008

(54) PYRIDAZINE DERIVATIVES AS LIGANDS FOR GABA RECEPTORS

(75) Inventors: Stephen Robert Fletcher, Bishops Stortford (GB); Angus Murray MacLeod, Bishops Stortford (GB); Monique Bodil Van Niel, Welwyn (GB); Kevin Wilson, West Newton, MA (US)

(73) Assignee: Merck Sharp & Dohme Ltd., Hoddesdon, Hertfordshire (GB)

( * ) Notice: Subject to any disclaimer, the term of this patent is extended or adjusted under 35 U.S.C. 154(b) by 283 days.

(21) Appl. No.: 10/524,006

(22) PCT Filed: Aug. 4, 2003

(86) PCT No.: PCT/GB03/03379

§ 371 (c)(1),
(2), (4) Date: Oct. 17, 2005

(87) PCT Pub. No.: WO2004/014891

PCT Pub. Date: Feb. 19, 2004

(65) Prior Publication Data

US 2006/0148809 A1 Jul. 6, 2006

(30) Foreign Application Priority Data

Aug. 13, 2002 (GB) .................. 0218876.1

(51) Int. Cl.
  A61K 31/501 (2006.01)
  C07D 401/04 (2006.01)
  C07D 403/04 (2006.01)
  C07D 405/04 (2006.01)
  C07D 409/04 (2006.01)
  C07D 237/14 (2006.01)
  C07D 237/20 (2006.01)
  A61P 25/28 (2006.01)

(52) U.S. Cl. .................. 514/252.02; 514/252.03; 544/238; 544/239

(58) Field of Classification Search ............... 544/238, 544/239; 514/252.02, 252.03
See application file for complete search history.

(56) References Cited

U.S. PATENT DOCUMENTS

| | | | |
|---|---|---|---|
| 3,705,157 A * | 12/1972 | Wiegand et al. | 544/238 |
| 4,432,979 A * | 2/1984 | Campbell | 514/252.03 |
| 4,985,444 A * | 1/1991 | Shiokawa et al. | 514/300 |
| 5,776,954 A * | 7/1998 | de Laszlo et al. | 514/340 |
| 6,200,982 B1 * | 3/2001 | Collins et al. | 514/277 |
| 6,255,305 B1 | 7/2001 | Broughton et al. | |
| 6,329,380 B1 * | 12/2001 | Goulet et al. | 514/260.1 |
| 6,903,086 B2 * | 6/2005 | Lopez-Tapia et al. | 514/183 |
| 7,005,432 B2 * | 2/2006 | Buettelmann et al. | 514/252.05 |
| 7,220,741 B2 * | 5/2007 | Peters et al. | 514/221 |
| 2004/0082551 A1 * | 4/2004 | Benson et al. | 514/150 |

FOREIGN PATENT DOCUMENTS

| | | | |
|---|---|---|---|
| JP | 61225182 | * | 10/1986 |
| WO | WO 0123383 | * | 4/2001 |
| WO | WO 0138332 | * | 5/2001 |
| WO | WO 02 076983 | | 10/2002 |
| WO | WO 02076983 | * | 10/2002 |
| WO | WO 03008405 | * | 1/2003 |

OTHER PUBLICATIONS

McKernan, et al., Nature Neuroscience, vol. 3, No. 6, Jun. 2000, pp. 587-592.*
Brambilla, et al., Molec. Psychiat. (2003) 8, pp. 721-737.*
Akahane, et al., Journal of Medicinal Chemistry (1999), 42(5), 779-783.*
Sauer, et al., Tetrahedron (1998), 54(17), 4297-4312.*
Heldmann, et al., Tetrahedron Letters (1997), 38(33), 5791-5794.*
Mertens, et al., Journal of Medicinal Chemistry (1990), 33(10), 2870-5.*
Yamazaki, et al., Chemical & Pharmaceutical Bulletin (1990), 38(1), 45-48.*
Haider, et al., Pharmazie (1989), 44(9), 598-601.*
Bourguignon, et al., Journal of Chemical Research, Synopses (1981), (4), 104-5.*
Szilagyi et al., European Journal of Medicinal Chemistry (1979), 14(5), 439-45.*
Adembri, et al., Journal of the Chemical Society, Perkin Transactions 1: Organic and Bio-Organic Chemistry (1972-1999) (1974), (9), 1022-6.*
Heinisch, Monatsh. Chem. (1973), 104(4), 953-62.*
Miyazawa, et al., Eisei Shikensho Hokoku (1963), No. 81, 98-100.*
Robba, Ann. Chim. (Paris) (1960), 380-414.*
Gundisch, et al., Bioorganic & Medicinal Chemistry (2001), 9(10), 2683-2691.*
Sauer, Jurgen et al: "Synthesis of 3,5-disubstituted pyridazines by regioselective '4+2! cycloadditions with ethynyltributyltin and subsequent replacement of the organotin substituent" Tetrahedron (1998), 54(17), 4297-4312.
Chem Abstracts XP002258329, 137:384849, Chemical Abstracts Service, Columbus Ohio, US; Minami, Nobuyoshi et al: "Preparation of 4-(4-pyridazinyl)pyrazole derivatives as p38MAP kinase(p3 mitogen-activated protein kinase) inhibitors".

* cited by examiner

*Primary Examiner*—Mark L. Berch
*Assistant Examiner*—Cecilia M Jaisle
(74) *Attorney, Agent, or Firm*—J. Eric Thies; William Krovatin

(57) ABSTRACT

A class of pyridazine derivatives, substituted in the 4-position by an optionally substituted heteroaromatic ring, being selective ligands for GABAA receptors, in particular having high affinity for the α2 and/or α3 and/or α5 subunit thereof, are accordingly of benefit in the treatment and/or prevention of adverse conditions of the central nervous system, including anxiety, convulsions and cognitive disorders.

4 Claims, No Drawings

PYRIDAZINE DERIVATIVES AS LIGANDS FOR GABA RECEPTORS

CROSS REFERENCE TO RELATED APPLICATIONS

This application is a U.S. National Phase application under 35 U.S.C. §371 of PCT Application No. PCT/GB2003/03379, filed Aug. 4, 2003, which claims priority under 35 U.S.C. § 119 from GB Application No. 0218876.1, filed Aug. 13, 2002.

The present invention relates to a class of substituted pyridazine derivatives and to their use in therapy. More particularly, this invention is concerned with pyridazine analogues which are substituted in the 4-position by an optionally substituted heteroaromatic ring. These compounds are ligands for $GABA_A$ receptors and are therefore useful in the therapy of deleterious neurological complaints.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six α subunits, four β subunits, three γ subunits, one δ subunit, one ε subunit and two ρ subunits.

Although knowledge of the diversity of the $GABA_A$ receptor gene family represents a huge step forward in our understanding of this ligand-gated ion channel, insight into the extent of subtype diversity is still at an early stage. It has been indicated that an α subunit, β subunit and a γ subunit constitute the minimum requirement for forming a fully functional $GABA_A$ receptor expressed by transiently transfecting cDNAs into cells. As indicated above, δ, ε and ρ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, α1β2γ2, α2βγ1, α2β2/3γ2, α3βγ2/3, α4βδ, α5β3γ2/3, α6βγ2, and α6βδ. Subtype assemblies containing an α1 subunit are present in most areas of the brain and are thought to account for over 40% of $GABA_A$ receptors in the rat. Subtype assemblies containing α2 and α3 subunits respectively are thought to account for about 25% and 17% of $GABA_A$ receptors in the rat. Subtype assemblies containing an α5 subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with β subunit and γ2. This is the most abundant $GABA_A$ receptor subtype, and is believed to represent almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3βγ2 subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which interact more favourably with the α2 and/or α3 subunit than with α1 will be effective in the treatment of anxiety with a reduced propensity to cause sedation. Moreover, agents which are inverse agonists of the α5 subunit are likely to be beneficial in enhancing cognition, for example in subjects suffering from dementing conditions such as Alzheimer's disease. Also, agents which are antagonists or inverse agonists at α1 might be employed to reverse sedation or hypnosis caused by α1 agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; Tourette's syndrome; speech disorders, including stuttering; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse or dependency, including alcohol withdrawal. Selective ligands for GABA$_A$ receptors may be beneficial in enhancing cognition, for example in subjects suffering from dementing conditions such as Alzheimer's disease; and may also be effective as pre-medication prior to anaesthesia or minor procedures such as endoscopy, including gastric endoscopy.

In addition, the compounds in accordance with the present invention may be useful as radioligands in assays for detecting compounds capable of binding to the human GABA$_A$ receptor.

The present invention provides a class of pyridazine derivatives which possess desirable binding properties at various GABA$_A$ receptor subtypes. The compounds in accordance with the present invention have good affinity as ligands for the α2 and/or α3 and/or α5 subunit of the human GABA$_A$ receptor. The compounds of this invention may interact more favourably with the α2 and/or α3 subunit than with the α1 subunit; and/or may interact more favourably with the α5 subunit than with the α1 subunit.

The compounds of the present invention are GABA$_A$ receptor subtype ligands having a binding affinity (K$_i$) for the α2 and/or α3 and/or α5 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 and/or α5 subunit relative to the α1 subunit. However, compounds which are not selective in terms of their binding affinity for the α2 and/or α3 and/or α5 subunit relative to the α1 subunit are also encompassed within the scope of the present invention; such compounds will desirably exhibit functional selectivity in terms of zero or weak (positive or negative) efficacy at the α1 subunit and (i) a full or partial agonist profile at the α2 and/or α3 subunit, and/or (ii) an inverse agonist profile at the α5 subunit.

The present invention provides a compound of formula I, or an N-oxide thereof or a pharmaceutically acceptable salt thereof:

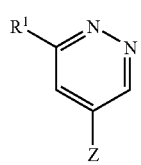

(I)

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole; or Z represents an optionally substituted six-membered heteroaromatic ring selected from pyridine, pyrazine, pyrimidine and pyridazine; or Z represents an optionally substituted fused bicyclic heteroaromatic moiety selected from benzofuran, benzothiophene, indole, indazole, benzimidazole and pyrazolo [1,5-α]pyridine;

R$^1$ represents hydrogen, hydrocarbon, a heterocyclic group, halogen, cyano, trifluoromethyl, nitro, —OR$^a$, —SR$^a$, —SO R$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$ or —CR$^a$=NOR$^b$; and R$^a$ and R$^b$ independently represent hydrogen, hydrocarbon or a heterocyclic group.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z.

Where Z in the compounds of formula I above represents a six-membered heteroaromatic ring, this ring may be optionally substituted by one or more substituents, typically by one or two substituents.

Suitably, the group Z is unsubstituted or monosubstituted.

Examples of optional substituents on the five-membered or six-membered or fused bicyclic heteroaromatic moiety as specified for Z include halogen, cyano, trifluoromethyl, C$_{1-6}$ alkyl, halo(C$_{1-6}$)alkyl, dihalo(C$_{1-6}$)alkyl, hydroxy(C$_{1-6}$) alkyl, C$_{1-6}$ alkoxy(C$_{1-6}$)alkyl, C$_{3-7}$ cycloalkyl, C$_{3-7}$ heterocycloalkyl, benzyl-tetrahydropyridinyl, oxy, hydroxy, C$_{1-6}$ alkoxy, methyltriazolyl(C$_{1-6}$)alkoxy, C$_{1-6}$ alkylthio, C$_{1-6}$ alkylsulphonyl, aminosulphonyl, C$_{2-4}$ alkylcarbonyl, C$_{2-6}$ alkoxycarbonyl, amino, C$_{1-6}$ alkylamino, di(C$_{1-6}$)alkylamino, C$_{2-6}$ alkylcarbonylamino, phenyl, (C$_{1-6}$)alkyl-phenyl, halophenyl, dihalophenyl, trihalophenyl, (fluoro)(methyl)phenyl, cyanophenyl, (cyano)(fluoro)phenyl, (cyano) (difluoro)phenyl, difluoromethyl-phenyl, trifluoromethylphenyl, (methyl)(trifluoromethyl)phenyl, (halo) (trifluoromethyl)phenyl, nitrophenyl, methoxyphenyl, (halo)(methoxy)phenyl, trifluoromethoxy-phenyl, (halo)(trifluoromethoxy)phenyl, methylenedioxy-phenyl, (C$_{2-6}$)alkylcarbonyl-phenyl, trifluorothio-phenyl, (C$_{1-6}$)alkylsulphonyl-phenyl, di(C$_{1-6}$)alkylaminocarbonyl-phenyl, di(C$_{1-6}$) alkylaminosulphonyl-phenyl, (halo)(morpholinylmethyl) phenyl, (halo)(pyridinyl)phenyl, imidazolyl-phenyl, thiadiazolyl-phenyl, methylthiadiazolyl-phenyl, (halo)(triazolyl)phenyl, methyltetrazolyl-phenyl and optionally substituted heteroaryl, the optional substituents on the heteroaryl moiety being typically selected from oxy, halogen, cyano and C$_{1-6}$ alkyl.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, indanyl, aryl and aryl(C$_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkenyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "$C_{1-6}$ alkoxy", "$C_{1-6}$ alkylamino" and "$C_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of $C_{3-7}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl, preferably phenyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

A typical heterocycloalkenyl group is dihydropyrrolyl.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, aryloxycarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$NR$^v$R$^w$ and —CH$_2$SO$_2$NR$^v$R$^w$, in which R$^v$ and R$^w$ independently represent hydrogen, $C_{1-6}$ alkyl, aryl or aryl($C_{1-6}$)alkyl.

The term "halogen" as used herein includes fluorine, chlorine, bromine and iodine, especially fluoro or chloro.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

The present invention includes within its scope tautomers of the compounds of formula I as defined above. For example, where Z represents an optionally substituted 2-hydroxypyridine moiety, this may co-exist, in whole or in part, with the corresponding 2-pyridone tautomer. It is to be understood that all such tautomers and mixtures thereof in any proportion are encompassed within the scope of the present invention.

Where the group Z represents an optionally substituted five-membered heteroaromatic ring, this is suitably a thiophene, thiazole or thiadiazole ring, either of which may be optionally substituted by one or, where possible, two substituents. In a particular embodiment, Z represents monosubstituted thiophene.

Where the group Z represents an optionally substituted six-membered heteroaromatic ring, this is suitably a pyridinyl or pyrimidinyl ring, either of which may be optionally substituted by one or more substituents, typically by one or two substituents. In one embodiment, Z represents monosubstituted pyridinyl. In another embodiment, Z represents monosubstituted pyrimidinyl.

Where the group Z represents an optionally substituted fused bicyclic heteroaromatic moiety, this is suitably pyrazolo[1,5-α]pyridine, which may be unsubstituted or substituted by one or more substituents, typically by one or two substituents.

Illustrative examples of optional substituents on the group Z include fluoro, chloro, bromo, iodo, cyano, trifluoromethyl, methyl, isopropyl, tert-butyl, chloromethyl, fluoropropyl (especially 2-fluoroprop-2-yl), difluoroethyl (especially 1,1-difluoroethyl), hydroxypropyl (especially 2-hydroxyprop-2-yl), methoxymethyl, cyclopentyl, pyrrolidinyl, morpholinyl, benzyl-tetrahydropyridinyl, oxy, hydroxy, methoxy, ethoxy, isopropoxy, tert-butoxy, methyltriazolylmethoxy, methylthio, ethylthio, methanesulphonyl, aminosulphonyl, acetyl, methoxycarbonyl, tert-butylamino, dimethylamino, acetylamino, phenyl, methylphenyl, isopropylphenyl, tert-butylphenyl, fluorophenyl, chlorophenyl, bromophenyl, difluorophenyl, dichlorophenyl, dibromophenyl, (chloro)(fluoro)phenyl, trifluorophenyl, trichlorophenyl, (fluoro)(methyl)phenyl, cyanophenyl, (cyano)(fluoro)phenyl, (cyano)(difluoro)phenyl, difluoromethylphenyl, trifluoromethyl-phenyl, (methyl)(trifluoromethyl)phenyl, (chloro)(trifluoromethyl)phenyl, nitrophenyl, methoxyphenyl, (fluoro)(methoxy)phenyl, trifluoromethoxy-phenyl, (fluoro)(trifluoromethoxy)phenyl, methylenedioxy-phenyl, acetylphenyl, trifluorothio-phenyl, methanesulphonyl-phenyl, ethanesulphonyl-phenyl, dimethylaminocarbonyl-phenyl, dimethylaminosulphonyl-phenyl, (fluoro)(morpholinylmethyl)phenyl, (fluoro)(pyridinyl) phenyl, imidazolyl-phenyl, thiadiazolyl-phenyl, methylthiadiazolyl-phenyl, (fluoro)(triazolyl)phenyl, methyltetrazolyl-phenyl, pyridinyl, oxypyridinyl, fluoropyridinyl, chloropyridinyl, cyanopyridinyl, methylpyridinyl, dimethyl-pyridinyl, pyridazinyl, pyrimidinyl, pyrazinyl, furyl, thienyl, cyanothienyl, pyrrolyl, pyrazolyl, oxazolyl, thiazolyl, isothiazolyl, imidazolyl, methylimidazolyl and triazolyl.

Particular substituents which may be attached to the group Z include trifluoromethyl, aminosulphonyl, methoxycarbonyl, fluorophenyl, cyanophenyl, (cyano)(fluoro)phenyl and pyridinyl.

Typical values of Z include aminosulphonyl-thienyl, methoxycarbonyl-thienyl, pyridinyl, fluorophenyl-pyridinyl, cyanophenyl-pyridinyl, (cyano)(fluoro)phenyl-pyridinyl, trifluoromethyl-pyrimidinyl, cyanophenyl-pyrimidinyl, pyridinyl-pyrimidinyl and pyrazolo[1,5-α]pyridinyl.

Typically, $R^1$ represents hydrocarbon, a heterocyclic group, —$OR^a$, —$NR^aR^b$ or —$CO_2R^a$.

Typical values of $R^a$ include $C_{1-6}$ alkyl, $C_{2-6}$ alkenyl, $C_{3-7}$ cycloalkyl and aryl($C_{1-6}$)alkyl (optionally substituted by $C_{1-6}$ alkoxy). Suitably, $R^a$ represents methyl, ethyl, n-propyl, isopropyl, allyl, cyclopropyl, cyclohexyl, benzyl or methoxybenzyl.

Typical values of $R^b$ include hydrogen and $C_{1-6}$ alkyl. Suitably, $R^b$ represents hydrogen or methyl, especially hydrogen.

Suitable values of $R^1$ include phenyl, halophenyl, dihalophenyl, $C_{1-6}$ alkoxyphenyl, cyanophenyl, (cyano)(halo)phenyl, $C_{3-7}$ heterocycloalkenyl, heteroaryl (optionally substituted by halo), $C_{1-6}$ alkoxy, $C_{2-6}$ alkenyloxy, aryl($C_{1-6}$)alkoxy, $C_{1-6}$ alkylamino, $C_{2-6}$ alkenylamino, $C_{3-7}$ cycloalkylamino, aryl($C_{1-6}$)alkylamino (optionally substituted by $C_{1-6}$ alkoxy) and $C_{2-6}$ alkoxycarbonyl.

Individual values of $R^1$ include phenyl, fluorophenyl, chlorophenyl, difluorophenyl, methoxyphenyl, cyanophenyl, (cyano)(fluoro)phenyl, dihydropyrrolyl, pyridinyl, fluoro-pyridinyl, pyrazinyl, furyl, thienyl, thiazolyl, triazolyl, methoxy, ethoxy, allyloxy, benzyloxy, methylamino, ethylamino, propylamino, isopropylamino, allylamino, cyclopropylamino, cyclohexylamino, benzylamino, methoxybenzyl-amino and ethoxycarbonyl.

In one embodiment, $R^1$ represents phenyl.

In another embodiment, $R^1$ represents fluorophenyl.

In a further embodiment, $R^1$ represents fluoro-pyridinyl.

A particular sub-class of compounds according to the invention is represented by the compounds of formula IA, and N-oxides thereof and pharmaceutically acceptable salts thereof:

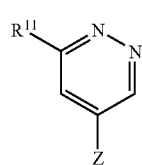

(IA)

wherein

Z is as defined above; and $R^{11}$ represents phenyl, halophenyl, dihalophenyl, $C_{1-6}$ alkoxyphenyl, cyanophenyl, (cyano)(halo)phenyl, $C_{3-7}$ heterocycloalkenyl, heteroaryl (optionally substituted by halo), $C_{1-6}$ alkoxy, $C_{2-6}$ alkenyloxy, aryl($C_{1-6}$)alkoxy, $C_{1-6}$ alkylamino, $C_{2-6}$ alkenylamino, $C_{3-7}$ cycloalkylamino, aryl($C_{1-6}$)alkylamino (optionally substituted by $C_{1-6}$ alkoxy) or $C_{2-6}$ alkoxycarbonyl.

Where $R^{11}$ represents heteroaryl, this group is suitably pyridinyl, pyrazinyl, furyl, thienyl, thiazolyl or triazolyl.

Itemised values of $R^{11}$ include phenyl, fluorophenyl, chlorophenyl, difluorophenyl, methoxyphenyl, cyanophenyl, (cyano)(fluoro)phenyl, dihydropyrrolyl, pyridinyl, fluoro-pyridinyl, pyrazinyl, furyl, thienyl, thiazolyl, triazolyl, methoxy, ethoxy, allyloxy, benzyloxy, methylamino, ethylamino, propylamino, isopropylamino, allylamino, cyclopropylamino, cyclohexylamino, benzylamino, methoxybenzyl-amino and ethoxycarbonyl.

In one embodiment, $R^{11}$ represents phenyl.

In another embodiment, $R^{11}$ represents fluorophenyl.

In a further embodiment, $R^{11}$ represents fluoro-pyridinyl.

One representative subset of the compounds of formula IA above is represented by the compounds of formula IIA, and N-oxides thereof and pharmaceutically acceptable salts thereof:

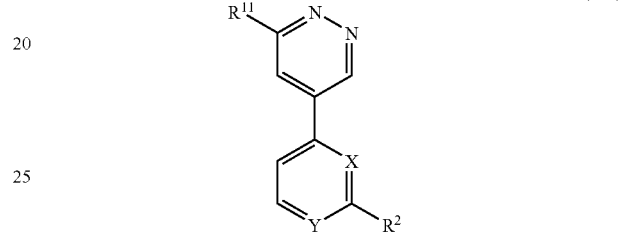

(IIA)

wherein

X represents CH and Y represents N; or

X represents N and Y represents CH or N;

$R^2$ represents hydrogen, halogen, cyano, trifluoromethyl, $C_{1-6}$ alkyl, halo($C_{1-6}$)alkyl, dihalo($C_{1-6}$)alkyl, hydroxy($C_{1-6}$)allyl, $C_{1-6}$ alkoxy($C_{1-6}$)alkyl, $C_{3-7}$ cycloalkyl, $C_{3-7}$ heterocycloalkyl, benzyl-tetrahydropyridinyl, $C_{1-6}$ alkoxy, methyltriazolyl($C_{1-6}$)alkoxy, $C_{1-6}$ alkylthio, $C_{1-6}$ alkylsulphonyl, aminosulphonyl, $C_{2-6}$ alkylcarbonyl, $C_{2-6}$ alkoxycarbonyl, amino, $C_{1-6}$ alkylamino, di($C_{1-6}$)alkylamino, $C_{2-6}$ alkylcarbonylamino, phenyl, ($C_{1-6}$)alkyl-phenyl, halophenyl, dihalophenyl, trihalophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (halo)(trifluoromethyl)phenyl, nitrophenyl, methoxyphenyl, (halo)(methoxy)phenyl, trifluoromethoxy-phenyl, (halo)(trifluoromethoxy)phenyl, methylenedioxy-phenyl, ($C_{2-6}$)alkylcarbonyl-phenyl, trifluorothio-phenyl, ($C_{1-6}$)alkylsulphonyl-phenyl, di($C_{1-6}$)alkylaminocarbonyl-phenyl, di($C_{1-6}$)alkylaminosulphonyl-phenyl, (halo)(morpholinylmethyl)phenyl, (halo)(pyridinyl)phenyl, imidazolyl-phenyl, thiadiazolyl-phenyl, methylthiadiazolyl-phenyl, (halo)(triazolyl)phenyl, methyltetrazolyl-phenyl or optionally substituted heteroaryl, the optional substituents on the heteroaryl moiety being selected from oxy, halogen, cyano and $C_{1-6}$ alkyl; and $R^{11}$ is as defined above.

Illustrative values of $R^2$ include hydrogen, fluoro, chloro, bromo, iodo, cyano, trifluoromethyl, methyl, isopropyl, tert-butyl, chloromethyl, fluoropropyl (especially 2-fluoroprop-2-yl), difluoroethyl (especially 1,1-difluoroethyl), hydroxypropyl (especially 2-hydroxyprop-2-yl), methoxymethyl, cyclopentyl, pyrrolidinyl, morpholinyl, benzyl-tetrahydropyridinyl, methoxy, ethoxy, isopropoxy, tert-butoxy, methyltriazolyl-methoxy, methylthio, ethylthio, methanesulphonyl, aminosulphonyl, acetyl, methoxycarbonyl, tert-butylamino, dimethylamino, acetylamino, phenyl, methylphenyl, isopropylphenyl, tert-butylphenyl, fluorophenyl, chlorophenyl, bromophenyl, difluorophenyl, dichlorophenyl, dibromophenyl, (chloro)(fluoro)phenyl, trifluorophenyl, trichlorophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (chloro)(trifluoromethyl)phenyl, nitrophenyl, methoxyphenyl, (fluoro)(methoxy)phenyl, trifluoromethoxy-phenyl, (fluoro)(trifluoromethoxy)phenyl, methylenedioxy-phenyl, acetylphenyl, trifluorothio-phenyl, methanesulphonyl-phenyl, ethanesulphonyl-phenyl, dimethylaminocarbonyl-phenyl, dimethylaminosulphonyl-phenyl, (fluoro)(morpholinylmethyl)phenyl, (fluoro)(pyridinyl)phenyl, imidazolyl-phenyl, thiadiazolyl-phenyl, methylthiadiazolyl-phenyl, (fluoro)(triazolyl)phenyl, methyltetrazolyl-phenyl, pyridinyl, oxypyridinyl, fluoropyridinyl, chloropyridinyl, cyanopyridinyl, methylpyridinyl, dimethyl-pyridinyl, pyridazinyl, pyrimidinyl, pyrazinyl, furyl, thienyl, cyanothienyl, pyrrolyl, pyrazolyl, oxazolyl, thiazolyl, isothiazolyl, imidazolyl, methylimidazolyl and triazolyl.

Particular values of $R^2$ include trifluoromethyl, fluorophenyl, cyanophenyl, (cyano)(fluoro)phenyl and pyridinyl.

An illustrative subset of the compounds of formula IIA above is represented by the compounds of formula IIB, and N-oxides thereof and pharmaceutically acceptable salts thereof:

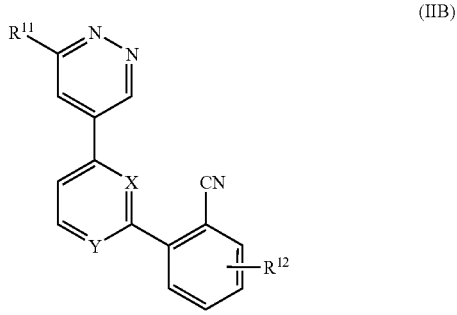

(IIB)

wherein

X, Y and $R^{11}$ are as defined above; and $R^{12}$ represents hydrogen or fluoro.

In one embodiment, $R^{12}$ represents hydrogen.

In another embodiment, $R^{12}$ represents fluoro, in which case the fluorine atom $R^{12}$ is favourably attached to the phenyl ring at the 4-, 5- or 6-position (relative to the cyano group at position 2).

In one embodiment of the compounds of formula IIA and IIB, X is CH and Y is N.

In another embodiment of the compounds of formula IIA and IIB, X is N and Y is CH.

In a further embodiment of the compounds of formula IIA and IIB, X and Y are both N.

Specific compounds within the scope of the present invention include:

3-phenyl-5-(pyridin-4-yl)pyridazine;
3-(6-phenylpyridazin-4-yl)thiophene-2-carboxylic acid methyl ester;
3-phenyl-5-(pyridin-3-yl)pyridazine;
5-(6-phenylpyridazin-4-yl)thiophene-2-sulfonic acid amide;
3-(6-phenylpyridazin-4-yl)pyrazolo[1,5-α]pyridine;
2-[2-(6-phenylpyridazin-4-yl)pyrimidin-4-yl]benzonitrile;
2-[6-(6-phenylpyridazin-4-yl)pyridin-2-yl]benzonitrile;
5-fluoro-2-[6-(6-phenylpyridazin-4-yl)pyridin-2-yl]benzonitrile;
4-fluoro-2-[6-(6-phenylpyridazin-4-yl)pyridin-2-yl]benzonitrile;
5-[2-(3-fluorophenyl)pyridin-4-yl]-3-phenylpyridazine;
3-phenyl-5-[2-(pyridin-4-yl)pyrimidin-4-yl]pyridazine;
3-phenyl-5-(2-trifluoromethylpyrimidin-4-yl)pyridazine;

and pharmaceutically acceptable salts thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the anxiolytic compounds of the invention is ideally 50 nM or less, preferably 10 nM or less, and more preferably 5 nM or less.

The anxiolytic compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670-678. The procedure will suitably be carried out utilising cultures of stably transfected eukaryotic cells, typically of stably transfected mouse Ltk-fibroblast cells.

The compounds according to the present invention may exhibit anxiolytic activity, as may be demonstrated by a positive response in the elevated plus maze and conditioned suppression of drinking tests (cf. Dawson et al., *Psychopharmacology*, 1995, 121, 109-117). Moreover, the compounds of the invention are likely to be substantially non-sedating, as may be confirmed by an appropriate result obtained from the response sensitivity (chain-pulling) test (cf. Bayley et al., *J. Psychopharmacol.*, 1996, 10, 206-213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492-501.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognition enhancement can be shown by testing the compounds in the Morris watermaze as reported by McNamara and Skelton, *Psychobiology*, 1993, 21, 101-108. Further details of relevant methodology are described in WO 96/25948.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

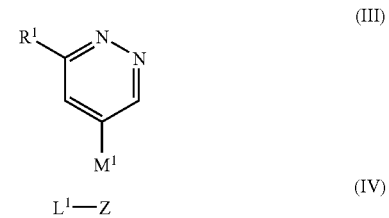

wherein Z and $R^1$ are as defined above, $L^1$ represents a suitable leaving group, and $M^1$ represents a boronic acid moiety —$B(OH)_2$ or a cyclic ester thereof formed with an organic diol, e.g. pinacol, 1,3-propanediol or neopentyl glycol, or $M^1$ represents —$Sn(Alk)_3$ in which Alk represents a $C_{1-6}$ alkyl group, typically n-butyl; in the presence of a transition metal catalyst.

The leaving group $L^1$ is typically a halogen atom, e.g. bromo or chloro.

The transition metal catalyst of use in the reaction between compounds III and IV is suitably tetrakis(triphenylphosphine)-palladium(0). The reaction is conveniently carried out at an elevated temperature in a solvent such as tetrahydrofuran, 1,4-dioxane or N,N-dimethylacetamide, typically in the presence of potassium phosphate, sodium carbonate, cesium carbonate or copper(I) iodide.

In an alternative procedure, the compounds according to the present invention may be prepared by a process which comprises reacting a compound of formula V with a compound of formula VI:

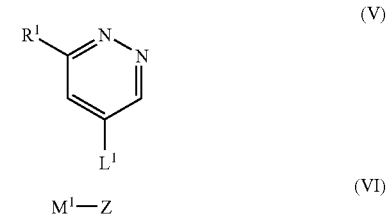

wherein Z, $R^1$, $L^1$ and $M^1$ are as defined above; in the presence of a transition metal catalyst; under conditions analogous to those described above for the reaction between compounds III and IV.

Where $M^1$ in the intermediates of formula III above represents —$Sn(Alk)_3$ in which Alk is n-butyl, this compound may be prepared by reacting a compound of formula V as defined above with tributyltin chloride.

The reaction is conveniently effected by stirring compound V with isopropylmagnesium chloride in a solvent such as tetrahydrofuran, with subsequent addition of tributyltin chloride.

In another procedure, the compounds according to the present invention wherein $R_1$ represents an aryl or heteroaryl moiety may be prepared by a process which comprises reacting a compound of formula VII with a compound of formula VIII:

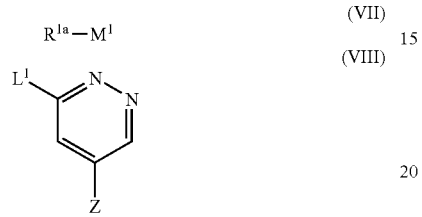

wherein Z, $L^1$ and $M^1$ are as defined above, and $R^{1a}$ represents an aryl or heteroaryl moiety; in the presence of a transition metal catalyst; under conditions analogous to those described above for the reaction between compounds III and IV.

In the compounds of formula VIII above, the leaving group $L^2$ is typically trifluoromethanesulphonyloxy (triflyloxy); or a halogen atom, e.g. chloro.

The transition metal catalyst of use in the reaction between compounds VII and VIII is suitably tetrakis(triphenylphosphine)-palladium(0), in which case the reaction is conveniently effected at an elevated temperature in a solvent such as N,N-dimethylacetamide, typically in the presence of potassium phosphate or in the presence of lithium chloride and copper(I) iodide. Alternatively, the transition metal catalyst may suitably be tris(dibenzylideneacetone)palladium(0), in which case the reaction is conveniently effected at an elevated temperature in a solvent such as 1,4-dioxane, typically in the presence of tri-tert-butylphosphine and cesium carbonate.

In a further procedure, the compounds according to the present invention wherein $R^1$ represents an aryl or heteroaryl moiety may be prepared by a process which comprises reacting a compound of formula IX with a compound of formula X:

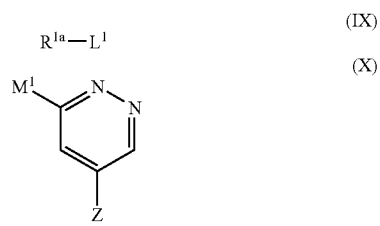

wherein Z, $R^{1a}$, $L^1$ and $M^1$ are as defined above; in the presence of a transition metal catalyst; under conditions analogous to those described above for the reaction between compounds III and IV.

The intermediates of formula X wherein $M^1$ represents —Sn(Alk)$_3$ and Alk represents $C_{1-6}$ alkyl, e.g. methyl, may be prepared by reacting a compound of formula VIII as defined above with a reagent of formula (Alk)$_3$Sn—Sn(Alk)$_3$. The reaction is conveniently effected in the presence of a transition metal catalyst, e.g. tetrakis(triphenylphosphine)palladium(0), with heating in a solvent such as 1,4-dioxane, typically in the presence of lithium chloride.

In a yet further procedure, the compounds according to the present invention wherein $R^1$ represents 1H-[1,2,3]triazol-4-yl may be prepared by a process which comprises reacting a compound of formula XI:

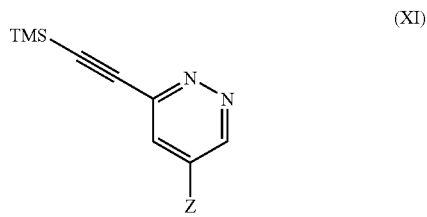

wherein Z is as defined above, and TMS is an abbreviation for trimethylsilanyl; with sodium azide.

The reaction is conveniently effected by stirring the reactants in a solvent such as N,N-dimethylformamide.

The intermediates of formula XI may be prepared by reacting a compound of formula VIII with TMS-acetylene, in the presence of a transition metal catalyst such as bis(triphenylphosphine)palladium(II) chloride. The reaction is conveniently effected by stirring in a solvent such as tetrahydrofuran, typically in the presence of triethylamine, triphenylphosphine and copper(I) chloride.

The compounds according to the present invention wherein $R^1$ represents —OR$^a$ may be prepared by a process which comprises reacting a compound of formula VIII as defined above with a compound of formula R$^a$—OH, wherein R$^a$ is as defined above. The reaction is conveniently carried out in the presence of a base such as sodium hydride or sodium ethoxide.

The compounds according to the present invention wherein $R^1$ represents —NR$^a$R$^b$ may be prepared by a process which comprises reacting a compound of formula VIII as defined above with a compound of formula H—NR$^a$R$^b$, wherein R$^a$ and R$^b$ are as defined above. The reaction is conveniently effected by stirring at an elevated temperature, typically in a solvent such as tetrahydrofuran.

The compounds according to the present invention wherein $R^1$ represents —CO$_2$R$^a$ may be prepared by a process which comprises reacting a compound of formula VIII as defined above with carbon dioxide and a compound of formula R$^a$—OH, wherein R$^a$ is as defined above; in the presence of a transition metal catalyst.

The transition metal catalyst of use in the foregoing reaction is ideally [1,1'-bis(diphenylphosphino)ferrocene]palladium(II) chloride, in which case the reaction is conveniently carried out at an elevated temperature in a solvent such as N,N-dimethylformamide, optionally in admixture with dichloromethane, typically in the presence of sodium acetate.

The intermediates of formula VIII wherein $L^1$ represents triflyloxy may be prepared by reacting a compound of formula XII:

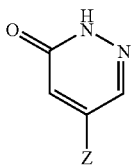

(XII)

wherein Z is as defined above; with N-phenyltriflylimide, typically in the presence of triethylamine, in a solvent such as dichloromethane.

Moreover, the intermediates of formula VIII wherein $L^1$ represents chloro may be prepared by treating the requisite compound of formula XII with phosphorus oxychloride at an elevated temperature.

The intermediates of formula XII may be prepared by reacting a compound of formula VI as defined above with a compound of formula XIII:

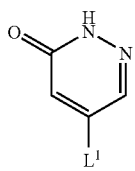

(XIII)

wherein $L^1$ is as defined above; in the presence of a transition metal catalyst; under conditions analogous to those described above for the reaction between compounds III and IV.

Alternatively, the intermediates of formula XII may be prepared by reacting a compound of formula XIV:

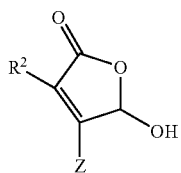

(XIV)

wherein Z and $R^2$ are as defined above; with hydrazine hydrate, typically in ethanol at reflux.

Where $L^1$ in the compounds of formula VIII above represents a halogen atom, these compounds correspond to compounds of formula I as defined above wherein $R^1$ represents halogen, and they therefore constitute compounds according to the invention in their own right.

Where they are not commercially available, the starting materials of formula IV, V, VI, VII, IX and XIII may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I initially obtained may be converted into the N-oxide derivative thereof by treatment with m-chloroperbenzoic acid. A compound of formula I initially obtained wherein the moiety Z is substituted by a halogen atom, e.g. bromo, may be converted into the corresponding compound wherein the moiety Z is substituted by an aryl or heteroaryl group, e.g. 2-cyanophenyl, 2-cyano-6-fluorophenyl or pyridin-3-yl, by treatment with the requisite aryl or heteroaryl boronic acid or cyclic ester thereof formed with an organic diol, e.g. 2-cyanophenylboronic acid, 3-fluoro-2-(4,4,5,5-tetramethyl-[1,3,2]dioxaborolan-2-yl)benzonitrile or pyridine-3-boronic acid-1,3-propanediol cyclic ester, in the presence of a transition metal catalyst such as tetrakis(triphenylphosphine)palladium(0), in which case the reaction is conveniently effected at an elevated temperature in a solvent such as N,N-dimethylacetamide, aqueous 1,2-dimethoxyethane, aqueous 1,4-dioxane or aqueous tetrahydrofuran, typically in the presence of potassium phosphate, sodium carbonate or cesium carbonate; or by treatment with the appropriate stannyl reagent, e.g. 2-tributylstannylbenzonitrile, in the presence of a transition metal catalyst such as dichloro[1,1'-bis(diphenylphosphino)ferrocene]palladium(II), in which case the reaction is conveniently effected at a elevated temperature in a solvent such as N,N-dimethylacetamide, typically in the presence of lithium chloride and copper(I) chloride; or by treatment with the appropriate stannyl reagent in the presence of a transition metal catalyst such as tetrakis(triphenylphosphine)palladium(0), in which case the reaction is conveniently accomplished at an elevated temperature in a solvent such as tetrahydrofuran or 1,4-dioxane, typically in the presence of copper(I) iodide; or, where the moiety Z in the desired compound of formula I is substituted by imidazol-1-yl, simply by treatment with imidazole in the presence of a strong base such as lithium hexamethyldisilazide (LiHMDS). A compound of formula I wherein the moiety Z is substituted by pyridinyl may be converted into the corresponding compound wherein Z is substituted by N-oxypyridinyl by treatment with meta-chloroperbenzoic acid. A compound of formula I wherein Z is substituted by a halogen atom, e.g. iodo, may be converted, by treatment with isopropylmagnesium chloride, into a Grignard reagent which may be reacted with an aldehyde such as acetaldehyde to afford a secondary alcohol, e.g. the 1-hydroxyethyl derivative; and this compound may in turn be treated with an oxidising agent, e.g. Dess-Martin periodinane, to afford the corresponding compound of formula I wherein Z is substituted by acetyl. The resulting acetyl derivative may be converted, by treatment with methylmagnesium chloride, into the corresponding compound wherein Z is substituted by 2-hydroxyprop-2-yl; and this compound may in turn be treated with (diethylamino)sulfur trifluoride (DAST) to afford the corresponding compound of formula I wherein Z is substituted by 2-fluoroprop-2-yl. A compound of formula I wherein $R^1$ represents —C(O-Alk$^1$)$_2$R$^a$ initially obtained, wherein Alk$^1$ represents $C_{1-6}$ alkyl, typically methyl or ethyl, may be converted into the corresponding compound of formula I wherein $R^1$ represents —COR$^a$ by hydrolysis with a mineral acid, typically aqueous hydrochloric acid. A compound wherein $R^1$ represents formyl may be reduced with sodium triacetoxyborohydride to the corresponding compound wherein $R^1$ represents hydroxymethyl. A compound of formula I wherein $R^1$ represents hydroxymethyl may be oxidised to the corresponding compound of formula I wherein $R^1$ represents formyl by treatment with manganese dioxide. The formyl derivative thereby obtained may be condensed with a hydroxylamine derivative of formula H$_2$N—OR$^b$ to provide a compound of formula I wherein $R^1$ represents —CH=NOR$^b$. Furthermore, a compound of formula I wherein $R^1$ represents —CH=NOH may be treated with triethylamine in the presence of 1,1'-carbonyldiimidazole to afford a corresponding compound of formula I wherein R¹ represents cyano. Alternatively, the compound of formula I wherein R¹ represents formyl may be reacted with a Grignard reagent of formula R$^a$MgBr to afford a compound of formula I wherein R¹ represents —CH(OH)R$^a$, and this compound may in turn be oxidised using manganese dioxide to the corresponding compound of formula I wherein R¹ represents —COR$^a$. The latter compound may then be condensed with a hydroxylamine derivative of formula H$_2$N—OR$^b$ to provide a compound of formula I wherein R¹ represents —CR$^a$═NOR$^b$. A compound of formula I wherein R¹ represents —CH(OH)R$^a$ may be converted into the corresponding compound of formula I wherein R¹ represents —CHFR$^a$ by treatment with DAST. Similarly, a compound of formula I wherein R¹ represents —COR$^a$ may be converted into the corresponding compound of formula I wherein R¹ represents —CF$_2$R$^a$ by treatment with DAST. A compound of formula I wherein R¹ represents amino may be converted into the corresponding compound of formula I wherein R¹ represents chloro by diazotisation, using sodium nitrite, followed by treatment with copper(I) chloride. A compound of formula I wherein R¹ represents —COCH$_3$ may be treated with thioacetamide in the presence of pyridinium tribromide to furnish the corresponding compound of formula I wherein R¹ represents 2-methylthiazol-5-yl. Moreover, a compound of formula I wherein R¹ is formyl may be treated with (p-tolylsulfonyl) methyl isocyanide (TosMIC) in the presence of potassium carbonate to afford the corresponding compound of formula I wherein R¹ represents oxazol-5-yl. A compound of formula I wherein R¹ represents hydroxymethyl may be treated with carbon tetrabromide and triphenylphosphine to afford the corresponding compound of formula I wherein R¹ represents bromomethyl, which may then be reacted (typically in situ) with the sodium salt of imidazole or 1H-[1,2,4]triazole to provide a compound of formula I wherein R¹ represents imidazol-1-ylmethyl or [1,2,4]triazol-1-ylmethyl respectively; or with the sodium salt of 1H-[1,2,3]triazole to provide a mixture of compounds of formula I wherein R¹ represents [1,2,3]triazol-1-ylmethyl and [1,2,3]triazol-2-ylmethyl; or with morpholine to provide a compound of formula I wherein R¹ represents morpholin-4-ylmethyl.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human GABA$_A$ receptors containing the α2 and/or α3 and/or α5 subunit stably expressed in Ltk⁻ cells.

Reagents

Phosphate buffered saline (PBS).
Assay buffer: 10 mM KH$_2$PO$_4$, 100 mM KCl, pH 7.4 at room temperature.
[$^3$H]-Flumazenil (18 nM for α1β3γ2 cells; 18 nM for α2β3γ2 cells; 10 nM for α3β3γ2 cells; 10 nM for α5β3γ2 cells) in assay buffer.
Flunitrazepam 100 μM in assay buffer.
Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.
50 μl of [$^3$H]-flumazenil (final concentration for α1β3γ2: 1.8 nM; for α2β3γ2: 1.8 nM; for α3β3γ2: 1.0 nM; for α5β3γ2: 1.0 nM).
50 μl of buffer or solvent carrier (e.g. 10% DMSO) if compounds are dissolved in 10% DMSO (total); test compound or flunitrazepam (to determine non-specific binding), 10 μM final concentration.
100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000-4000 dpm for total counts and less than 200 dpm for non-specific binding if using liquid scintillation counting, or 1500-2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 and/or α5 subunit of the human GABA$_A$ receptor of 100 nM or less.

EXAMPLE 1

3-Phenyl-5-(pyridin-4-yl)pridazine

3-Phenyl-5-(tri-n-butylstannyl)pyridazine (110 mg, 0.247 mmol), 4-bromopyridine hydrochloride (72 mg, 0.370 mmol) and Pd(PPh$_3$)$_4$ (10 mg) in THF (2 ml) were combined and heated to 150° C. for 60 min in a Smith Synthesiser microwave reactor (Personal Chemistry, Uppsala, Sweden). The reaction was diluted with $CH_2Cl_2$ (6 ml) and $NH_4Cl$ (2 ml) then poured into PTFE (5 μM) fritted syringe barrels. The organic phase was collected and concentrated while loading onto silica. The compound was purified by dry flash column chromatography to give the title compound as a white solid (40 mg). $\delta_H$ (400 MHz, $d^6$ DMSO) 7.36-7.63 (3H, m), 8.10 (2H, dd, J 1.8 and 4.5), 8.32 (2H, m), 8.62 (1H, d, J 2.0), 8.80-8.82 (2H, dd, J 1.8 and 4.5), 9.71 (2H, d, J 2.0); m/z ($ES^+$) 234 ($MH^+$).

EXAMPLE 2

3-(6-Phenylpyridazin-4-yl)thiophene-2-carboxylic Acid Methyl Ester

3-Phenyl-5-(tri-n-butylstannyl)pyridazine (50 mg, 0.11 mmol), methyl 3-bromothiophene-2-carboxylate (30 mg) and $Pd(PPh_3)_4$ (5 mg) in THF (2 ml) were combined and heated to 150° C. for 600 seconds in a Smith Synthesizer microwave reactor. The reaction was diluted with $CH_2Cl_2$ (6 ml) and $H_2O$ (2 ml) then poured into PTFE (5 μM) fritted syringe barrels. The organic phase was collected and concentrated to leave 85 mg of crude product. Part of the sample was purified by HPLC with mass triggered collection of fractions to give the title compound (3.9 mg). $\delta_H$ (400 MHz, $d^6$ DMSO) 3.73 (3H, s), 7.52-7.62 (4H, m), 8.10 (1H, d, J 8.0), 8.22 (2H, dd, J 1.6 and 8.0), 8.35 (1H, d, J 4.0), 9.33 (1H, d, J 4.0); m/z ($ES^+$) ($MH^+$) 297.

EXAMPLES 3 TO 12

The compounds in Table 1 were prepared, using the heteroaryl halides shown, in an analogous manner to that described in Examples 1 and 2 and were purified by HPLC with mass triggered fraction collection or recrystallisation from MeOH-EtOAc, $CH_2Cl_2$ or $CH_2Cl_2$-$^i$PrOH.

TABLE 1

| EX. NO. | STARTING HETEROARYL HALIDE | PRODUCT | $\delta_H$ (400 MHz, $d^6$ DMSO) | m/z ($ES^+$) |
|---|---|---|---|---|
| 3 | (3-bromopyridine) | 3-Phenyl-5-(pyridin-3-yl)-pyridazine | 7.58-7.60 (5H, m), 8.19 (2H, d, J 8), 8.27 (2H, d, J 8), 8.49 (1H, d, J 2), 9.61 (1H, d, J 2). | 234 |
| 4 | (5-bromothiophene-2-sulfonamide) | 5-(6-Phenyl-pyridazin-4-yl)thiophene-2-sulfonic acid amide | 7.54-7.64 (3H, m), 7.70 (1H, d, J 3.9), 7.91 (2H, s), 8.11 (1H, d, J 4), 8.26-8.29 (2H, m), 8.46 (1H, d, J 2.3), 9.60 (1H, d, J 2.3). | 318 |
| 5 | (3-bromopyrazolo[1,5-α]pyridine) | 3-(6-Phenyl-pyridazin-4-y)-pyrazolo[1,5-α]pyridine | 7.27-7.30 (2H, m), 7.57-7.64 (3H, m), 8.20 (2H, m), 8.78 (1H, d, J 4), 8.87 (1H, m), 9.21 (1H, s), 9.28-9.30 (1H, m). | 273 |
| 6 | (2-(2-bromopyrimidin-4-yl)benzonitrile) | 2-[2-(6-Phenyl-pyridazin-4-yl)pyrimidin-4-yl]-benzonitrile | 7.58-7.65 (3H, m), 7.81-7.86 (1H, m), 7.94-7.98 (1H, m), 8.16-8.18 (1H, m), 8.26 (1H, d, J 5.1), 8.28-8.30 (2H, m), 8.31-8.33 (1H, m), 9.12 (1H, d, J 2.0), 9.28 (1h, d, J 5.1), 10.12 (1H, d, J 2.0). | 336 |

TABLE 1-continued

| EX. NO. | STARTIING HETEROARYL HALIDE | PRODUCT | δ$_H$ (400 MHz, d$^6$ DMSO) | m/z (ES$^+$) |
|---|---|---|---|---|
| 7 | | 2-[6-(6-Phenyl-pyridazin-4-yl)pyridin-2-yl]-benzonitrile | 7.58-7.65 (3h, m), 7.70-7.75 (1H, m), 7.87-7.92 (1H, m), 8.10-8.15 (3H, m), 8.12 (1H, dd, J 6.3, 1.8), 8.25-8.33 (2H, m), 8.50-8.55 (1H, m), 9.00 (1H; d, J 2.1), 10.08 (1H, d, J 2.1). | 335 |
| 8 | | 5-Fluoro-2-[6-(6-phenyl-pyridazin-4-yl)pyridin-2-yl]-benzonitrile | 7.55-7.65 (4H, m), 8.16-8.22 (1H, m), 8.15-8.22 (2H, m), 8.27-8.33 (3H, m), 8.55-8.60 (1H, m), 9.00 (1H, d, J 1.8), 10.08 (1H, d, J 1.8). | 353 |
| 9 | | 4-Fluoro-2-[6-(6-phenyl-pyridazin-4-yl)pyridin-2-yl]-benzonitrile | 7.55-7.64 (3H, m), 7.76-7.82 (1H, m), 8.09-8.12 (2H, m), 8.21 (1H, dd, J 5.6, 8.8), 8.25-8.32 (3H, m), 8.53 (1H, d, J 7.7), 8.98 (1H, d, J 1.8), 10.06 (1H, d, J 2.1). | 353 |
| 10 | | 5-[2-(3-Fluoro-phenyl)-pyridin-4-yl]-3-phenyl-pyridazine | 7.31-7.36 (1H, m), 7.57-7.65 (4H, m), 8.08-8.13 (3H, m), 8.32-8.35 (2H, m), 8.66 (1H, s), 8.74 (1H, d, J 2.3), 8.90 (1H, d, J 5.1), 9.84 (1H, d, J 2.3). | 328 |
| 11 | | 3-Phenyl-5-[2-(pyridin-4-yl)-pyrimidin-4-yl]pyridazine | 7.54-7.87 (6H, m), 7.98 (1H, dd, J 1.4, 7.6), 8.27-8.38 (3H, m), 8.48 (1H, dd, J 2.3, 6.7), 8.55 (1H, d, J 2.3), 9.69 (1H, d, J 2.3). | 370 |
| 12 | | 3-Phenyl-5-(2-trifluoro-methyl-pyrimidin-4-yl)pyridazine | 7.58-7.66 (3H, m), 8.32 (2H, dd, J 1.4, 8.0), 8.84 (1H, d, J 5.1), 8.89 (1H, d, J 2.3), 9.37 (1H, d, J 5.5), 9.91 (1H, d, J 4). | 303 |

The invention claimed is:
1. A compound of the formula IIB:

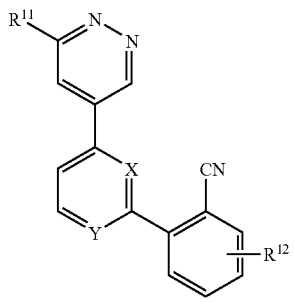

wherein:

X is CH and Y is N; or X is N and Y is CH or N;

$R^{11}$ is selected from the group consisting of: phenyl, halophenyl, dihalophenyl, $C_{1-6}$ alkoxyphenyl, cyanophenyl, (cyano)(halo)phenyl, $C_{3-7}$ heterocycloalkenyl, heteroaryl (which is unsubstituted or substituted by halo), $C_{1-6}$ alkoxy, $C_{2-6}$ alkenyloxy, aryl($C_{1-6}$)alkoxy, $C_{1-6}$ alkylamino, $C_{2-6}$ alkenylamino, $C_{3-7}$ cycloalkylamino, aryl($C_{1-6}$)alkylamino (which is unsubstituted or substituted by $C_{1-6}$ alkoxy), and $C_{2-6}$ alkoxycarbonyl;

$R^{12}$ is hydrogen or fluoro, or a pharmaceutically acceptable salt thereof.

2. A compound which is selected from the group consisting of:

3-phenyl-5-(pyridin-4-yl)pyridazine;

3-(6-phenylpyridazin-4-yl)thiophene-2-carboxylic acid methyl ester;

3-phenyl-5-(pyridin-3-yl)pyridazine;

5-(6-phenylpyridazin-4-yl)thiophene-2-sulfonic acid amide;

3-(6-phenylpyridazin-4-yl)pyrazolo[1,5-α]pyridine;

2-[2-(6-phenylpyridazin-4-yl)pyrimidin-4-yl]benzonitrile;

2-[6-(6-phenylpyridazin-4-yl)pyridin-2-yl]benzonitrile;

5-fluoro-2-[6-(6-phenylpyridazin-4-yl)pyridin-2-yl]benzonitrile;

4-fluoro-2-[6-(6-phenylpyridazin-4-yl)pyridin-2-yl]benzonitrile;

5-[2-(3-fluorophenyl)pyridin-4-yl]-3-phenylpyridazine;

3-phenyl-5-[2-(pyridin-4-yl)pyrimidin-4-yl]pyridazine; and 3-phenyl-5-(2-trifluoromethylpyrimidin-4-yl)pyridazine;

or a pharmaceutically acceptable salt thereof.

3. A pharmaceutical composition comprising the compound of claim 1, or a pharmaceutically acceptable salt thereof, and a pharmaceutically acceptable carrier.

4. A pharmaceutical composition comprising the compound of claim 2, or a pharmaceutically acceptable salt thereof, and a pharmaceutically acceptable carrier.

* * * * *